United States Patent
Shirazian et al.

(10) Patent No.: US 12,161,512 B2
(45) Date of Patent: Dec. 10, 2024

(54) SYSTEMS AND METHODS FOR INTEGRATING IMAGERY CAPTURED BY DIFFERENT IMAGING MODALITIES INTO COMPOSITE IMAGERY OF A SURGICAL SPACE

(71) Applicant: Intuitive Surgical Operations, Inc., Sunnyvale, CA (US)

(72) Inventors: Pourya Shirazian, Menlo Park, CA (US); Mahdi Azizian, San Jose, CA (US); A. Jonathan McLeod, Sunnyvale, CA (US); Daniel Proksch, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 352 days.

(21) Appl. No.: 17/615,001

(22) PCT Filed: May 29, 2020

(86) PCT No.: PCT/US2020/035125
§ 371 (c)(1),
(2) Date: Nov. 29, 2021

(87) PCT Pub. No.: WO2020/243432
PCT Pub. Date: Dec. 3, 2020

(65) Prior Publication Data
US 2022/0218435 A1 Jul. 14, 2022

Related U.S. Application Data

(60) Provisional application No. 62/855,755, filed on May 31, 2019.

(51) Int. Cl.
*A61B 90/00* (2016.01)
*A61B 34/00* (2016.01)
*G06T 15/20* (2011.01)

(52) U.S. Cl.
CPC ............ *A61B 90/37* (2016.02); *A61B 34/25* (2016.02); *G06T 15/205* (2013.01);
(Continued)

(58) Field of Classification Search
CPC ....... A61B 34/25; A61B 34/30; A61B 8/5261; A61B 6/5247; A61B 90/37;
(Continued)

(56) References Cited

U.S. PATENT DOCUMENTS

2002/0140709 A1 10/2002 Sauer et al.
2006/0267977 A1* 11/2006 Barfuss .................... G06T 7/33
345/419

(Continued)

FOREIGN PATENT DOCUMENTS

CN 1864633 A 11/2006
CN 102781336 A 11/2012
(Continued)

OTHER PUBLICATIONS

Lerotic M., et al., "pq-space Based Non-Photorealistic Rendering for Augmented Reality," Medical Image Computing and Computer-Assisted Intervention, 2007, vol. 10 (Pt 2), pp. 102-109.
(Continued)

*Primary Examiner* — Xilin Guo

(57) ABSTRACT

An exemplary system accesses imagery of a surgical space captured by different imaging modalities and, based on the accessed imagery, generates composite imagery that includes integrated representations of the surgical space as captured by the different imaging modalities. An exemplary composite image includes a representation of the surgical space as captured by a first imaging modality augmented with an integrated representation of the surgical space as captured by a second imaging modality. The integrated representation of the surgical space as captured by the
(Continued)

second imaging modality may be selectively movable and may be generated based on first imagery of the surgical space captured by the first imaging modality and second imagery of the surgical space captured by the second imaging modality in a manner that provides a visually realistic appearance of depth.

20 Claims, 10 Drawing Sheets

(52) U.S. Cl.
CPC ... *A61B 2090/365* (2016.02); *A61B 2090/373* (2016.02); *A61B 2090/374* (2016.02); *A61B 2090/3762* (2016.02); *A61B 2090/378* (2016.02); *G06T 2210/41* (2013.01)

(58) Field of Classification Search
CPC ...... A61B 2034/2059; A61B 2090/064; A61B 2034/105; A61B 2090/3762; A61B 2090/364; A61B 2090/371; A61B 2090/374; A61B 2090/373; A61B 2090/365; A61B 2090/378; A61B 2034/2065; A61B 34/20; G06T 15/205; G06T 19/00; G06T 15/20; G06T 2210/41; G06T 2219/028; G06V 2201/034; G06V 10/16
See application file for complete search history.

(56) References Cited

U.S. PATENT DOCUMENTS

| | | | | |
|---|---|---|---|---|
| 2008/0030578 | A1* | 2/2008 | Razzaque | A61B 1/0005 348/E7.086 |
| 2013/0322717 | A1* | 12/2013 | Bar-Shalev | G06T 7/74 382/131 |
| 2014/0303491 | A1 | 10/2014 | Shekhar et al. | |
| 2017/0007350 | A1 | 1/2017 | Popovic et al. | |
| 2019/0060001 | A1* | 2/2019 | Kohli | A61B 34/20 |

FOREIGN PATENT DOCUMENTS

| | | |
|---|---|---|
| CN | 102999938 A | 3/2013 |
| CN | 103371870 A | 10/2013 |
| CN | 105979900 A | 9/2016 |
| CN | 108882854 A | 11/2018 |
| WO | WO-2007047782 A2 | 4/2007 |
| WO | WO-2019006028 A1 | 1/2019 |

OTHER PUBLICATIONS

International Preliminary Report on Patentability for Application No. PCT/US2020/035113 mailed on Dec. 9, 2021, 9 pages.
International Preliminary Report on Patentability for Application No. PCT/US2020/035125 mailed on Dec. 9, 2021, 9 pages.
International Search Report and Written Opinion for Application No. PCT/US2020/035113, mailed Sep. 18, 2020, 11 pages.
International Search Report and Written Opinion for Application No. PCT/US2020/035125, mailed Sep. 22, 2020, 11 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Bichlmeier C., "Immersive, Interactive and Contextual In-situ Visualization for Medical Applications," Computer Science, Engineering, Medicine, 2010, pp. 1-189, Retrieved from the Internet: [URL: https://mediatum.ub.tum.de/doc/977862/977862.pdf].
Office Action for Chinese Application No. CN202080052031.5, mailed Jul. 5, 2024, 36 pages.
Office Action for Chinese Application No. CN202080052031.5, mailed Jul. 29, 2023, 28 pages.

* cited by examiner

SYSTEMS AND METHODS FOR INTEGRATING IMAGERY CAPTURED BY DIFFERENT IMAGING MODALITIES INTO COMPOSITE IMAGERY OF A SURGICAL SPACE

RELATED APPLICATIONS

The present application is a U.S. National Stage Application under 35 U.S.C. § 371 of International Application No. PCT/US2020/035125, filed on May 29, 2020, which claims priority to U.S. Provisional Patent Application No. 62/855,755, filed on May 31, 2019, the contents of which are hereby incorporated by reference in their entirety.

BACKGROUND INFORMATION

During a surgical procedure, an endoscope may be used to capture endoscopic imagery of a surgical space. The endoscopic imagery may be presented to a surgeon by way of a display device so that the surgeon may visualize the surgical space while performing the surgical procedure. An endoscope is one imaging modality that is used to capture imagery of the surgical space.

In some scenarios, one or more additional imaging modalities may be used to capture additional imagery of the surgical space that may also be presented to the surgeon. For example, an ultrasound scan, a computerized tomography (CT) scan, and a magnetic resonance imaging (MRI) scan are other imaging modalities that may be used to capture imagery of the surgical space.

Imagery captured by different imaging modalities may be presented to the surgeon such that the surgeon may visualize the surgical space while performing the surgical procedure. However, there remains room to improve technologies for processing and presenting imagery captured by different surgical space imaging modalities.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions and a processor communicatively coupled to the memory and configured to execute the instructions to determine an image render viewpoint from which to render an image of a surgical space; determine, from a perspective of the image render viewpoint, a position of an augmentation region relative to the surgical space, the augmentation region selectively movable relative to the surgical space; generate a composite image of the surgical space from the perspective of the image render viewpoint and based on the determined position of the augmentation region relative to the surgical space, and direct a display device to display the composite image. The composite image may include: the augmentation region at the determined position of the augmentation region relative to the surgical space; outside the augmentation region, a representation of a first portion of the surgical space as captured by a first imaging modality; and inside the augmentation region, a representation of a second portion of the surgical space as captured by a second imaging modality, the representation of the second portion of the surgical space generated based on first imagery of the surgical space captured by the first imaging modality and second imagery of the surgical space captured by the second imaging modality.

Another exemplary system includes a memory storing instructions and a processor communicatively coupled to the memory and configured to execute the instructions to access first imagery of a surgical space captured by a first imaging modality; access second imagery of the surgical space captured by a second imaging modality, the second imaging modality different from the first imaging modality; generate a composite image of the surgical space based on the first imagery captured by the first imaging modality and the second imagery captured by the second imaging modality; and direct a display device to display the composite image. The composite image may include: a representation of a first portion of the surgical space as captured by the first imaging modality, the representation of the first portion of the surgical space generated based on the first imagery captured by the first imaging modality; an augmentation region integrated within the representation of the first portion of the surgical space; and, inside the augmentation region, a representation of a second portion of the surgical space as captured by the second imaging modality, the representation of the second portion of the surgical space including a composition of imagery of the surgical space captured by the second imaging modality modified by a feature of imagery of the surgical space captured by the first imaging modality.

An exemplary method includes a computing system determining an image render viewpoint from which to render an image of a surgical space; determining, from a perspective of the image render viewpoint, a position of an augmentation region relative to the surgical space, the augmentation region selectively movable relative to the surgical space; generating a composite image of the surgical space from the perspective of the image render viewpoint and based on the determined position of the augmentation region relative to the surgical space; and directing a display device to display the composite image. The composite image may include: the augmentation region at the determined position of the augmentation region relative to the surgical space; outside the augmentation region, a representation of a first portion of the surgical space as captured by a first imaging modality; and, inside the augmentation region, a representation of a second portion of the surgical space as captured by a second imaging modality, the representation of the second portion of the surgical space generated based on first imagery of the surgical space captured by the first imaging modality and second imagery of the surgical space captured by the second imaging modality.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
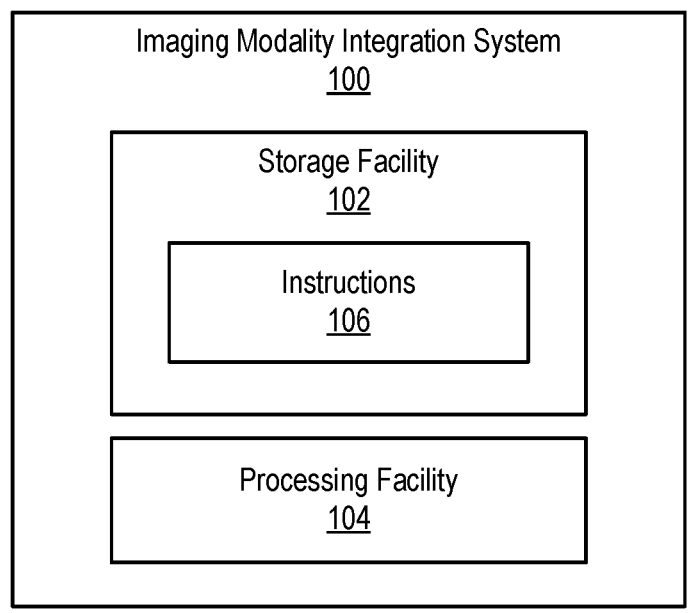
FIG. 1 illustrates an exemplary imaging modality integration system according to principles described herein.

Systems and methods for integrating imagery captured by different imaging modalities into composite imagery of a surgical space are described herein. In certain examples, an imaging modality integration system may be configured to integrate imagery captured by different imaging modalities by generating composite imagery that includes integrated representations of a surgical space as captured by multiple different imaging modalities. For example, the imaging modality integration system may be configured to generate a composite image that includes a representation of a first portion of the surgical space as captured by a first imaging modality and an integrated representation of a second portion of the surgical space as captured by a second imaging modality. The imaging modality integration system may be configured to integrate the representation of the second portion of the surgical space with the representation of the first portion of the surgical space in a manner that augments imagery of the surgical space as captured by one imaging modality (e.g., endoscopic imaging) with imagery of the surgical space as captured by a second imaging modality (e.g., ultrasound, CT, or MRI imaging).

In certain examples, the imaging modality integration system may be configured to generate the representation of the second portion of the surgical space based on first imagery of the surgical space captured by the first imaging modality and second imagery of the surgical space captured by the second imaging modality. For example, the representation of the second portion of the surgical space may be generated to include a composition of the second imagery of the surgical space and a feature of the first imagery of the surgical space. For instance, to produce the representation of the second portion of the surgical space, the second imagery of the surgical space may be combined with slope imagery representing gradient information extracted from the first imagery of the surgical space. Such a composition may produce a visually realistic appearance (e.g., an appearance of depth that facilitates depth perception) of the representation of the second portion of the surgical space integrated with the representation of the first portion of the surgical space. In certain examples, the composition is generated based on actual, organic colors of the first imagery and the second imagery, without using artificial or non-photorealistic colors. Examples of how the representation of the second portion of the surgical space may be generated and integrated with the representation of the first portion of the surgical space are described herein.

In certain examples, the first imaging modality may include endoscopic imaging (e.g., imaging by an endoscope) that captures endoscopic imagery of surface anatomy included in a surgical space, and the second imaging modality (e.g., ultrasound, CT, or MRI imaging) may capture imagery of subsurface anatomy included in the surgical space. In such examples, the imaging modality integration system may be configured to generate composite imagery that includes a representation of a first portion of the surgical space that is generated based on the endoscopic imagery of surface anatomy as captured by an endoscope and an integrated representation of a second portion of the surgical space that is generated based on the imagery of the subsurface anatomy as captured by the second imaging modality. The representation of the second portion of the surgical space may be generated to include a composition of the imagery of the subsurface anatomy as captured by the second imaging modality and a feature of the endoscopic imagery of the surface anatomy as captured by the endoscope. For instance, the imagery of the subsurface anatomy as captured by the second imaging modality may be combined with slope imagery extracted from the endoscopic imagery to produce the representation of the second portion of the surgical space. Such a composition may produce a visually realistic appearance (e.g., an appearance of depth that facilitate depth perception) of the imaged subsurface anatomy relative to the imaged surface anatomy when the representations are integrated in a composite image.

In certain examples, the second portion of the surgical space may be dynamically selected by way of user input to a computer-assisted surgical system or automatically by the computer-assisted surgical system (e.g., by performing an automatic scan). For example, the imaging modality integration system may be configured to provide an augmentation region (e.g., a virtual object representing an augmentation region) that is selectively movable relative to the surgical space based on user input to the computer-assisted surgical system or based on automatic movement controlled by the computer-assisted surgical system (e.g., as part of an automatic scan). At any given time during a surgical procedure, the imaging modality integration system may be configured to determine a position of the augmentation region relative to the surgical space and to use the determined position of the augmentation region relative to the surgical space to determine the first and second portions of the surgical space to be used to generate a composite image of the surgical space. For example, the imaging modality integration system may be configured to identify the first portion of the surgical space to be a portion of the surgical space that is outside of the augmentation region from a perspective of an image render viewpoint, and to identify the second portion of the surgical space to be a portion of the surgical space that is inside the determined position of the augmentation region from the perspective of the image render viewpoint. The imaging modality integration system may use the identified first and second portions of the surgical space to generate a composite image of the surgical space. As described herein, the composite image may include integrated representations of the first and second portions of the surgical space as respectively captured by first and second imaging modalities.

To illustrate an example, the imaging modality integration system may be configured to determine an image render viewpoint from which to render an image of a surgical space, determine, from a perspective of the image render viewpoint, a position of an augmentation region relative to the surgical space, and generate a composite image of the surgical space from the perspective of the image render viewpoint and based on the determined position of the augmentation region relative to the surgical space such that the composite image includes: the augmentation region (e.g., a representation of the augmentation region) at the determined position of the augmentation region relative to the surgical space; outside the augmentation region, a representation of a first portion of the surgical space as captured by a first imaging modality; and, inside the augmentation region, a representation of a second portion of the surgical space as captured by a second imaging modality. The representation of the second portion of the surgical space may be generated in any of the ways described herein and may be based on first imagery of the surgical space captured by the first imaging modality and second imagery of the surgical space captured by the second imaging modality.

Systems and methods described herein may provide various advantages and benefits. For example, systems and methods described herein may integrate imagery captured by different imaging modalities into composite imagery of a surgical space in a manner that produces, within the composite imagery, an integrated and visually realistic appearance of imagery of the surgical scene as captured by the different imaging modalities. Systems and methods described herein may present the generated composite imagery to a user of a computer-assisted surgical system, such as a surgeon utilizing the computer-assisted surgical system to perform a surgical procedure. The presented composite imagery may be visually realistic and intuitive to the surgeon, may reduce the complexity of the surgical procedure for the surgeon (e.g., by eliminating the need for the surgeon to mentally align imagery of the surgical space that is presented separately in a non-integrated manner), may allow the surgeon to concurrently, conveniently, and intuitively visualize surface and subsurface anatomy integrated in composite imagery, and/or may allow the surgeon to provide input to conveniently and dynamically select a portion of a surgical space that is to be augmented such that the selected portion may be viewed using a different imaging modality than is used to view another portion of the surgical space (e.g., by selecting a portion of the surgical space at which imagery of subsurface anatomy is displayed as an augmentation to imagery of surface anatomy being displayed). Additionally, composite imagery that is generated based on actual, organic colors of captured imagery, without using artificial or non-photorealistic colors, may be more realistic in appearance (e.g., facilitate better depth perception) compared to composite imagery that is generated based on artificial or non-photorealistic colors.

These and other advantages and benefits of systems and methods described herein will be made apparent herein.

FIG. 1 illustrates an exemplary imaging modality integration system 100 ("system 100") configured to integrate imagery captured by different imaging modalities, including by using the captured imagery to generate composite imagery that includes integrated representations of portions of a surgical space as captured by the different imaging modalities. System 100 may be included in, implemented by, or connected to one or more components of a computer-assisted surgical system. For example, system 100 may be implemented by one or more components of a computer-assisted surgical system. As another example, system 100 may be implemented by a stand-alone computing system communicatively coupled to a computer-assisted surgical system. An exemplary computer-assisted surgical system is described further below.

As shown in FIG. 1, system 100 may include a storage facility 102 and a processing facility 104 selectively and communicatively coupled to one another. Each of facilities 102 and 104 may include or be implemented by one or more physical computing devices including hardware and/or software components such as processors, memories, storage drives, communication interfaces, instructions stored in memory for execution by the processors, and so forth. Although facilities 102 and 104 are shown to be separate facilities in FIG. 1, facilities 102 and 104 may be combined into fewer facilities, such as into a single facility, or divided into more facilities as may serve a particular implementation. In some examples, each of facilities 102 and 104 may be distributed between multiple devices and/or multiple locations as may serve a particular implementation.

Storage facility 102 may maintain (e.g., store) executable data used by processing facility 104 to perform one or more of the operations described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with integrating imagery captured by different imaging modalities into composite imagery of a surgical space. For example, processing facility 104 may be configured to generate composite imagery that includes integrated representations of a surgical space as captured by multiple different imaging modalities. For instance, processing facility 104 may be configured to generate a composite image that includes a representation of a first portion of the surgical space as captured by a first imaging modality and a representation of a second portion of the surgical space as captured by a second imaging modality. Processing facility 104 may be configured to integrate the representation of the second portion of the surgical space with the representation of the first portion of the surgical space such that the representations become an integrated whole within the composite image. Processing facility 104 may perform the integration in any of the ways described herein and in a manner that augments imagery of the surgical space as captured by one imaging modality (e.g., endoscopic imaging) with imagery of the surgical space as captured by a second imaging modality (e.g., ultrasound, CT, or MRI imaging).

These and other operations that may be performed by processing facility 104 are described herein. In the description that follows, any references to operations performed by system 100 may be understood to be performed by processing facility 104 of system 100.

Figure 2:
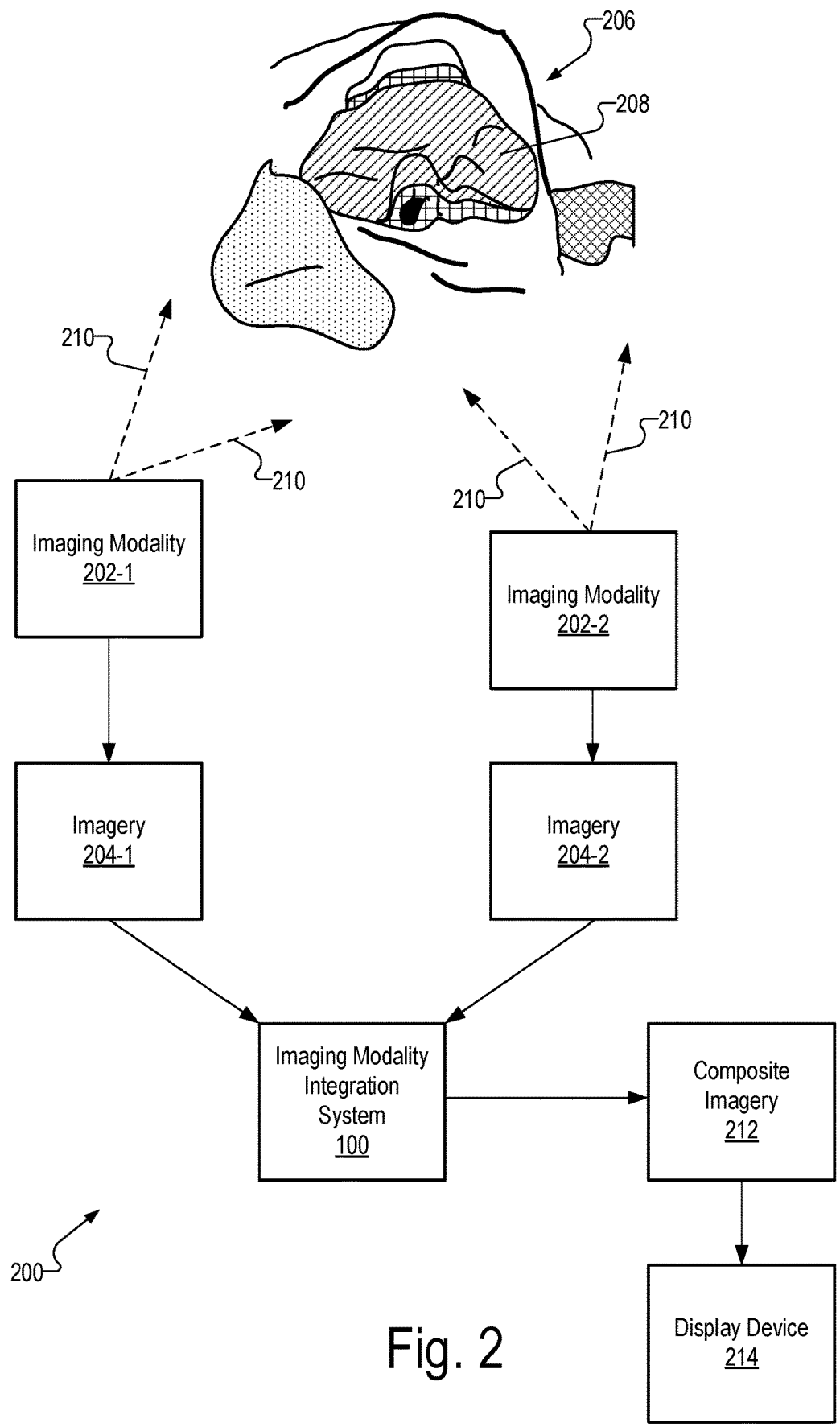
FIG. 2 illustrates the imaging modality integration system of FIG. 1 configured to generate composite imagery of a surgical space based on imagery captured by different imaging modalities according to principles described herein.

FIG. 2 illustrates a configuration 200 in which system 100 is configured to generate composite imagery of a surgical space based on imagery captured by different imaging modalities. As shown, configuration 200 may include multiple imaging modalities 202 (e.g., imaging modalities 202-1 and 202-2) configured to capture imagery 204 (e.g., imagery 204-1 captured by imaging modality 202-1 and imagery 204-2 captured by imaging modality 202-2) of a surgical space 206.

Surgical space 206 may include any volumetric space associated with a surgical procedure. For example, surgical space 206 may include any part or parts of a body of a patient, such as anatomy 208 (e.g., tissue, etc.) of the patient in a space associated with the surgical procedure. Surgical space 206 may, in certain examples, be entirely disposed within the patient and may include a space within the patient near where a surgical procedure is planned to be performed, is being performed, or has been performed. For example, for a minimally invasive surgical procedure being performed on tissue internal to a patient, surgical space 206 may include the tissue, anatomy underlying the tissue, as well as space around the tissue where, for example, surgical instruments being used to perform the surgical procedure are located. In other examples, surgical space 206 may be at least partially disposed external to the patient. For instance, for an open surgical procedure being performed on a patient, part of surgical space 206 (e.g., tissue being operated on) may be internal to the patient while another part of surgical space 206 (e.g., a space around the tissue where one or more surgical instruments may be disposed) may be external to the patient. Surgical space 206 may include a real workspace in which a surgical procedure is performed, such as an actual, real-world workspace associated with a patient and in which one or more surgical instruments are used to perform the surgical procedure on the patient.

As used herein, a surgical procedure may include any medical procedure, including any diagnostic or treatment procedure in which manual and/or instrumental techniques are used on a patient to investigate or treat a physical condition of the patient. A surgical procedure may refer to any phases of a medical procedure, such as preoperative, operative (i.e., intraoperative), and postoperative phases of a surgical procedure.

Imaging modalities 202 may be configured and/or used to capture imagery 204 of surgical space 206. Such a capture is represented by dashed lines 210 in FIG. 2. Imaging modalities 202 may each capture imagery 204 of surgical space 206 in any suitable manner and at any suitable time. Accordingly, one or more imaging modalities 202 may capture imagery 204 of surgical space 206 during one or more preoperative, intraoperative, and/or postoperative phases of a surgical procedure.

Imaging modalities 202 may include any set of different imaging modalities that may be used to capture imagery of a surgical space. Examples of imaging modalities 204 include, without limitation, endoscopic imaging by an endoscope, ultrasound imaging by an ultrasound machine, CT imaging by a CT machine, and MRI imaging by an MRI machine. Any suitable additional or alternative imaging modalities may be used in other examples. In certain implementations, imaging modality 202-1 may include endoscopic imaging by an endoscope, and imaging modality 202-2 may include any different imaging modality such as ultrasound imaging by an ultrasound machine, CT imaging by a CT machine, or MRI imaging by an MRI machine. In such implementations, imaging modality 202-1 may capture imagery 204-1 that is endoscopic imagery of surgical space 206, and imaging modality 202-2 may capture imagery 204-2 that is ultrasound imagery, CT imagery, or MRI imagery of surgical space 206.

In certain examples, imaging modality 202-1 may be configured to capture imagery of surface anatomy included in surgical space (e.g., an outer surface of tissue included in the surgical space), and imaging modality 202-2 may be configured to capture imagery of subsurface anatomy included in the surgical space (e.g., subsurface tissue that is behind the outer surface of tissue included in the surgical space). For example, imaging modality 202-1 may include endoscopic imaging by an endoscope that captures images of surface tissue within a patient, and imaging modality 202-1 may include ultrasound, CT, or MRI imaging that captures images of subsurface tissue that, from the perspective of the endoscope, is behind and hidden from the view of the endoscope by the surface tissue within the patient.

As mentioned, imaging modalities 202 may each capture imagery 204 of surgical scene 206 at any suitable time, such as during any phase(s) of a surgical procedure. In certain examples, imaging modalities 202 may concurrently capture imagery 204 of surgical space 206. For instance, imaging modality 202-1 may capture endoscopic imagery during a surgical procedure (e.g., during an operative phase of the surgical procedure), and imaging modality 202-1 may concurrently capture another type of imagery during the surgical procedure. In other examples, imaging modalities 202 may capture imagery 204 of surgical space 206 at different times and/or during different phases of the surgical procedure. For instance, imaging modality 202-1 may capture endoscopic imagery during an operative phase of the surgical procedure, and imaging modality 202-2 may capture another type of imagery during a preoperative phase of the surgical procedure.

Imagery 204 of surgical space 206 may include images of surgical space 206 captured by imaging modalities 202. For example, imagery 204 may include endoscopic images, ultrasound images, CT images, MRI images, and/or any other suitable form of images of surgical space 206. Imagery 204 may include any suitable type of images represented by data in any suitable data format. For example, imagery 204 may include still-frame images, video, color images, infrared images, and/or any other type of images that may visually represent surgical space 206. An image captured by an imaging modality may include a grid of pixels having values (e.g., color values, brightness values, etc.) representative of an appearance of surgical space 206 as captured by the imaging modality. Color values for pixels in a captured image may represent actual, organic colors of the surgical space as captured by an imaging modality.

Additionally or alternatively, imagery 204 may include one or more models of surgical space 206 that are generated based on imaging performed by an imaging modality. For example, imagery 204 may include a three-dimensional (3D) model of surgical space 206 that is generated based on imaging performed by an imaging modality, such as imaging performed by an ultrasound machine, a CT machine, an MRI machine, or other suitable imaging modality. The 3D model may be a full volumetric model that includes voxels (i.e., volumetric pixels) having values (e.g., color values, brightness values, etc.) representative of an appearance of surgical space 206 at 3D points within the model. Such a volumetric model may facilitate any slice of the 3D model being identified and used by system 100 to produce an image of the slice of the 3D model. Color values for pixels in the slice image may represent actual, organic colors of the surgical space as captured by an imaging modality.

While FIG. 2 depicts two imaging modalities 202-1 and 202-2 respectively capturing imagery 204-1 and 204-2 that are provided as input to system 100, other examples may include any suitable number and/or configuration of multiple, different imaging modalities that capture imagery that is provided as input to system 100 for use in generating composite imagery of surgical space 206. For example, three or more different imaging modalities may capture imagery that is input to system 100 for use in generating composite imagery of surgical space 206.

System 100 may generate composite imagery 212 of surgical space 206 based on imagery 204 captured by imaging modalities 202. System 100 may do this in any of the ways described herein to generate a composite image that includes integrated representations of portions of surgical space 206 as captured by different imaging modalities 202. Examples of such composite images and how the composite images may be generated are described herein.

System 100 may direct a display device 214 to display composite imagery 212. For example, system 100 may provide data representative of composite imagery 212 to display device 214, which may be configured to display composite imagery 212 for viewing by a user of a computer-assisted surgical system. Display device 214 may include any device capable of receiving and processing imagery data to display one or more images. To this end, display device 214 may include one or more display screens on which images may be displayed. In certain examples, display device 214 may be a component of or communicatively connected to a computer-assisted surgical system.

Figure 3:
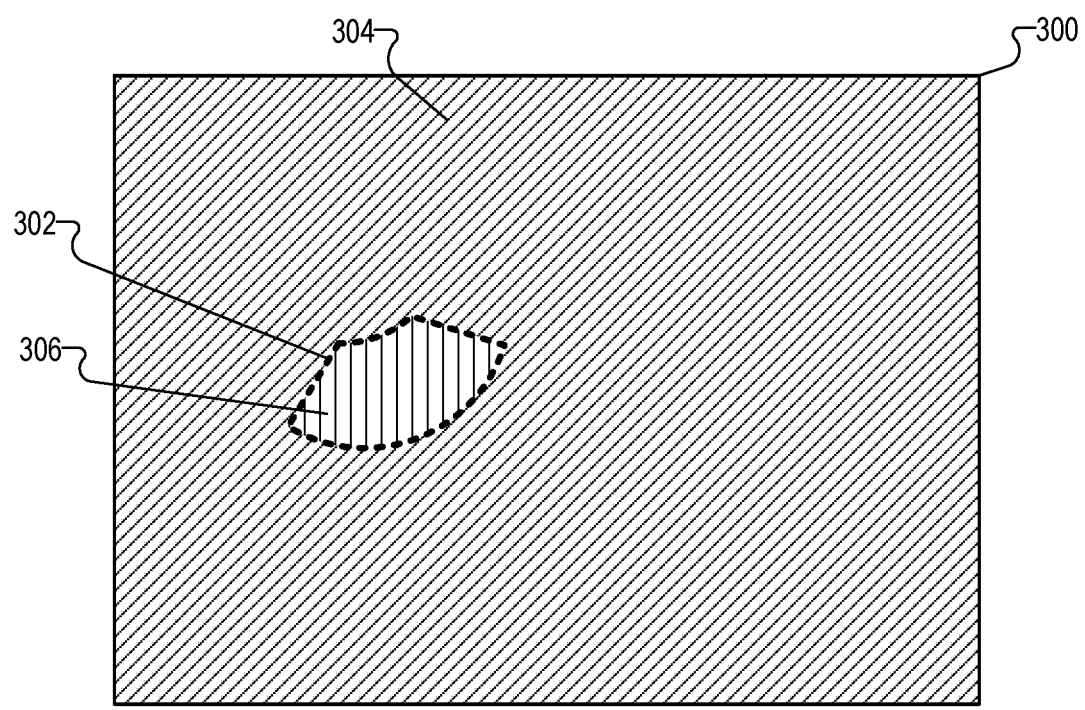
FIG. 3 illustrates an exemplary composite image of a surgical space according to principles described herein.

FIG. 3 illustrates an exemplary composite image 300 that may be generated by system 100 and displayed by a display device. Composite image 300 may be an image of a surgical space and may include a representation 302 of an augmentation region positioned relative to the surgical space. The positioning of augmentation region 302 within composite image 300 may represent and/or be determined from a position of augmentation region 302 (e.g., a position of a virtual object representing augmentation region 302) relative to the surgical space. Examples of positioning of augmentation region 302 relative to the surgical space are described herein.

Augmentation region 302 may be any suitable shape that defines an area within composite image 300. For example, augmentation region 302 may be a circle, an oval, a quadrilateral (e.g., a rectangle, a fan), a triangle, or any other suitable shape.

The positioning of augmentation region 302 within composite image 300 may define two portions of composite image 300—a first portion that is outside augmentation region 302, and a second portion that is inside augmentation region 302. In the first portion of composite image 300, which is outside augmentation region 302, composite image 300 may include a representation 304 of the first portion of the surgical space as captured by a first imaging modality. For example, representation 304 may include imagery of the surgical space captured by the first imaging modality, such as imagery 204-1 captured by first imaging modality 202-1. In the second portion of composite image 300, which is inside augmentation region 302, composite image 300 may include a representation 306 of the second portion of the surgical space as captured by a second imaging modality. For example, representation 306 may include imagery of the surgical space captured by the second imaging modality and modified by a feature of imagery of the surgical space captured by the first imaging modality, such as imagery 204-2 captured by second imaging modality 202-2 and modified by a feature of imagery 204-1 captured by first imaging modality 202-1. Accordingly, representation 306 of the second portion of the surgical space may be generated based on both imagery 204-1 and imagery 204-2 and may include a composition of imagery 204-2 and a feature (e.g., gradient information) of imagery 204-1. As indicated herein, this composition may create a visually realistic appearance of depth of representation 306 when representation 306 is integrated with representation 304 in composite image 300. In FIG. 3, representation 304 is illustrated to include diagonal lines, and representation 306 is illustrated to include vertical lines to indicate that representations 304 and 306 represent the surgical space as captured by different imaging modalities.

In composite image 300, representation 304 of the first portion of the surgical space as captured by the first imaging modality is augmented with integrated representation 306 of the second portion of the surgical space as captured by the second imaging modality. Accordingly, a surgeon and/or other surgical team member viewing composite image 300 may concurrently visualize integrated representations 304 and 306 of portions of the surgical space as captured by different imaging modalities. Because representation 306 is positionally integrated within representation 304, the surgeon may visualize the surgical space as captured by the different imaging modalities without having to mentally align the representations 304 and 306 to one another and the surgical space as would be required if representations 304 and 306 were presented separately and were not positionally integrated with one another.

In certain examples, augmentation region 302 may be movable relative to the surgical space by way of user input to a computer-assisted surgical system. The computer-assisted surgical system may be configured to receive any suitable user input that may be used to move augmentation region 302 relative to the surgical space. Such input may include actuation of buttons, movement of a controller (e.g., a joystick controller, a master control, etc.), movement of a surgical instrument connected to the computer-assisted surgical system (e.g., movement of an ultrasound probe or other surgical instrument from which augmentation region 302 is projected), and/or any other suitable user input.

Such movement of augmentation region 302 may allow a user of the computer-assisted surgical system to select, on the fly during a surgical procedure, a particular portion of the surgical space that is to be viewed as captured by the second imaging modality instead of as captured by the first imaging modality. This may allow a surgeon to dynamically "spotlight" a select portion of the surgical space in order to view the select portion as captured by the second imaging modality. For example, representation 304 may represent surface anatomy of a patient as captured by an endoscope, and representation 306 may represent subsurface anatomy of the patient as captured by a different imaging modality such as an ultrasound, CT, or MRI device. In this example, the surgeon may position augmentation region 302 to view subsurface anatomy at a select portion of the surgical space, while still viewing surface anatomy at another portion of the surgical space. In such implementations, augmentation region 302 may function as a virtual cut-away region (e.g., a virtual cut plane) that may be used by a surgeon to select a portion of a representation of surface anatomy to be virtually cut away from view to reveal a representation of subsurface anatomy located behind the surface anatomy (e.g., a virtual cut plane into a preoperative 3D model of the surgical space that is registered with an endoscopic view of the surgical space).

Movement of augmentation region 302 relative to the surgical space may include movement in any suitable direction(s) relative to the surgical space. For example, the movement may include lateral movement that pans augmentation region 302 across an image of the surgical space. Additionally or alternatively, the movement may include depth movement that changes a distance of augmentation region 302 from the perspective viewpoint from which the image of the surgical space is rendered. Such depth movement of augmentation region 302 may position augmentation region 302 at different depths relative to the surgical space, which position may be used to identify a slice of a virtual representation of the surgical space to be rendered (e.g., a slice of a 3D model that is mapped to a virtual representation of the surgical space). Such freedom of movement of augmentation region 302 may provide a user of the computer-assisted surgical system flexibility to select, on the fly during a surgical procedure, a particular portion of the surgical space to be augmented and imagery to be used for the augmentation.

To generate a composite image of a surgical space, system 100 may determine an image render viewpoint from which to render an image of the surgical space and, from a perspective of the image render viewpoint, a position of an augmentation region relative to the surgical space. System 100 may generate a composite image of the surgical space from the perspective of the image render viewpoint and based on the determined position of the augmentation region relative to the surgical space. The composite image may include: the augmentation region at the determined position of the augmentation region relative to the surgical space; outside the augmentation region, a representation of a first portion of the surgical space as captured by a first imaging modality; and inside the augmentation region, a representation of a second portion of the surgical space as captured by a second imaging modality. The representation of the second portion of the surgical space may be generated in any of the ways described herein and may be based on first imagery of the surgical space captured by the first imaging modality and second imagery of the surgical space captured by the second imaging modality.

Figure 4:
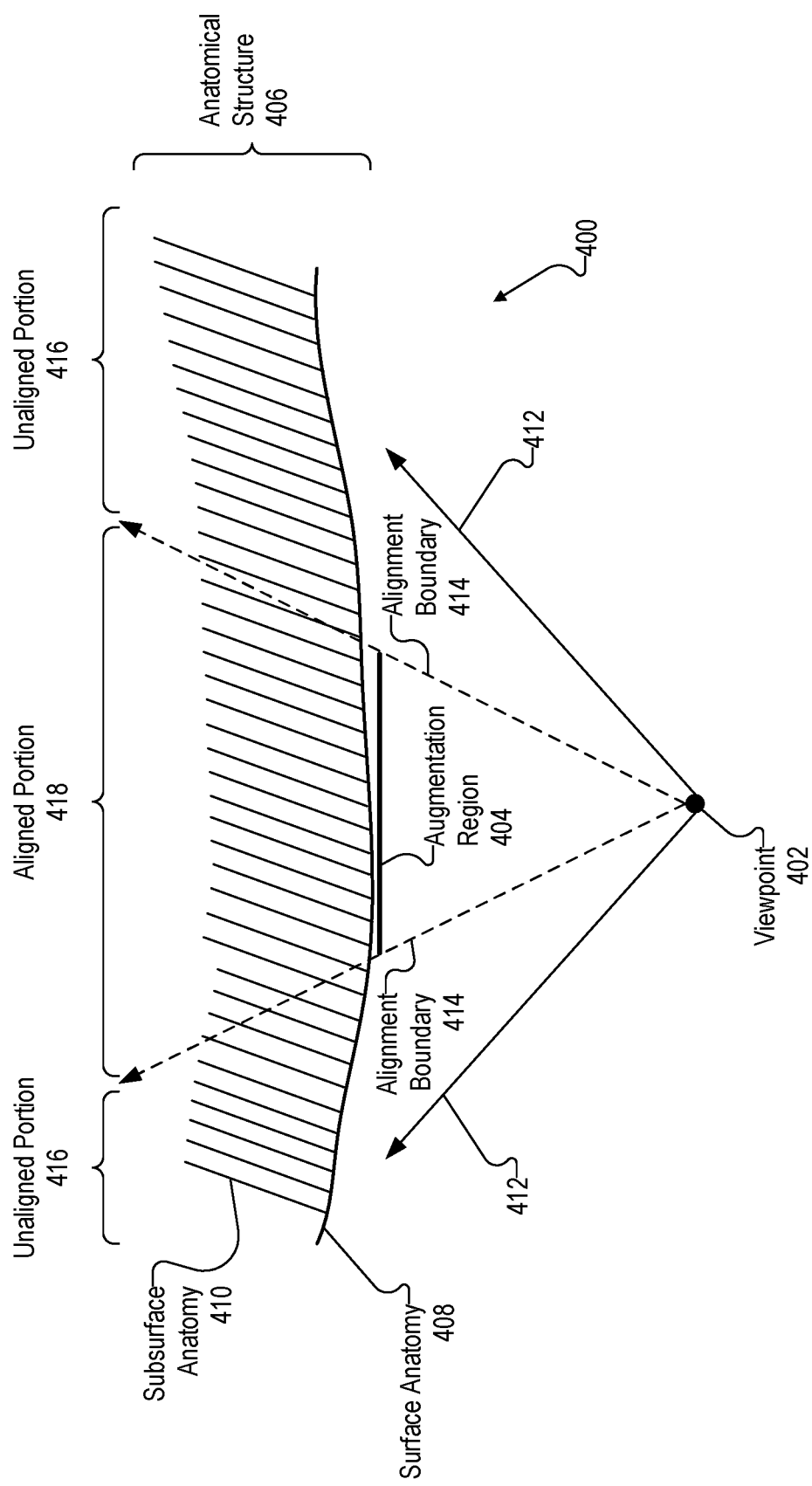
FIG. 4 illustrates an exemplary positioning of an image render viewpoint and an augmentation region relative to a surgical space according to principles described herein.

FIG. 4 illustrates an exemplary depiction of a surgical space 400 with an image render viewpoint 402 and augmentation region 404 positioned relative to surgical space 400. While the depiction shows a two-dimensional (2D) view, principles described with respect to the 2D view also apply to a 3D view of a surgical space with an image render viewpoint 402 and an augmentation region 404 positioned relative to the surgical space.

As shown in FIG. 4, surgical space 400 includes an anatomical structure 406, which includes surface anatomy 408 and subsurface anatomy 410. Subsurface anatomy 410 may include any anatomy positioned behind surface anatomy 408 from the perspective of image render viewpoint 402 and/or hidden from view from the perspective of image render viewpoint 402 by surface anatomy 408. In certain examples, surface anatomy 408 may include an outer layer of tissue of a patient, and subsurface anatomy 410 may include anatomy embedded within the outer layer of tissue.

Image render viewpoint 402 ("viewpoint 402") may be any viewpoint from which an image of surgical space 400 may be rendered. Viewpoint 402 may include an actual viewpoint of an imaging modality such as an endoscope (e.g., a viewpoint of one or more cameras of an endoscope). Alternatively, viewpoint 402 may include a virtual viewpoint corresponding to an actual viewpoint of an imaging modality such as an endoscope. Viewpoint 402 may be associated with and/or represent intrinsic and extrinsic properties of an imaging device such as one or more cameras of an endoscope. Viewpoint 402 may have a field of view within which an image of surgical space 400 may be rendered. A space within solid-line arrows 412 extending from viewpoint 400 represents a field of view of viewpoint 402.

As shown, viewpoint 402 is located at a position relative to surgical space 400 and defines a perspective from which an image of surgical space 400 may be rendered. The position of viewpoint 402 illustrated in FIG. 4 is exemplary only. Viewpoint 402 may be located at any position relative to surgical space 400 from which an image of surgical space 400 may be rendered.

Augmentation region 404 may be positioned relative to surgical space 400 to define a portion of surgical space 400 that is to be augmented. Augmentation region 404 may be defined to include any suitable shape, area, or volume that may be positioned relative to surgical space 400 to delineate, from the perspective of viewpoint 402, a portion of surgical space 400 that is to be augmented. In FIG. 4, augmentation region 404 is represented as a side view of a planar shape, which may be a circle, oval, quadrilateral, or any other suitable planar shape.

In certain examples, augmentation region 404 may be a virtual object or a view of a virtual object from the perspective of viewpoint 402. For example, a virtual object may be defined and positioned relative to surgical space. The virtual object may be a 2D or 3D object. The virtual object may be movable relative to surgical space 400 by way of user input to a computer-assisted surgical system.

At a given point in time, system 100 may determine positions of viewpoint 402 and augmentation region 404 relative to surgical space 400 and generated a composite image of surgical space 400 based on the determined positions of viewpoint 402 and augmentation region 404 relative to surgical space 400. In the composite image, a first portion of surgical space 400 may be represented with imagery as captured by a first imaging modality, and a second portion of surgical space 400 may be represented with imagery as captured by a second imaging modality.

To this end, system 100 may use the determined positions of viewpoint 402 and augmentation region 404 relative to surgical space 400 to define the first and second portions of surgical space 400. To illustrate, FIG. 4 shows dashed lines extending from viewpoint 402 and intersecting boundaries of augmentation region 404 to define alignment boundaries 414.

Portions of surgical space 400 that are outside of a space within alignment boundaries 414 are referred to as unaligned portions 416 of surgical space 400 because these portions are not aligned with augmentation region 404 from the perspective of viewpoint 402. Unaligned portions 416 of surgical space 400 may make up a first portion of surgical space 400 in a composite image of surgical space 400.

A portion of surgical space 400 that is inside a space within alignment boundaries 414 is referred to as an aligned portion 418 of surgical space 400 because this portion is aligned with augmentation region 404 from the perspective of viewpoint 402. Aligned portion 418 of surgical space 400 may make up a second portion of surgical space 400 in the composite image of surgical space 400.

In the composite image of surgical space 400, a representation of the first portion of surgical space 400 (a representation of unaligned portions 416 of surgical space 400) may be generated based on imagery captured by a first imaging modality. For example, the first imaging modality may include an endoscope positioned at viewpoint 402 to capture endoscopic imagery of surgical space 400, and the representation of the first portion of surgical space 400 may include endoscopic imagery of surface anatomy 408 in the unaligned portions 416 of surgical space 400.

In the composite image of surgical space 400, a representation of the second portion of surgical space 400 (a representation of aligned portion 418 of surgical space 400) may be generated based on imagery captured by a second imaging modality that is different from the first imaging modality. For example, the second imaging modality may include an ultrasound, CT, or MRI device that captured ultrasound, CT, or MRI imagery of surgical space 400, and the representation of the second portion of surgical space 400 may include ultrasound, CT, or MRI imagery of surface anatomy 408 or subsurface anatomy 410 in the aligned portion 418 of surgical space 400. In examples in which the representation of the second portion of surgical space 400 is generated based on imagery of subsurface anatomy 410 in the aligned portion 418 of surgical space 400, the imagery may be of subsurface anatomy 410 and any depth or depths behind the surface anatomy 408. In some implementations, a depth of imagery of the subsurface anatomy 410 as captured by the second imaging modality may be selected (e.g., on the fly during a surgical procedure) by user input to a computer-assisted surgical system, such as by user input that moves augmentation region 404 in a manner that changes the distance between viewpoint 402 and augmentation region 404 and/or moves augmentation region 404 to a select depth within subsurface anatomy 410.

As described herein, the representation of the second portion of surgical space 400 in the composite image may be generated based on imagery captured by the second imaging modality and imagery captured by the first imaging modality. For example, the representation of the second portion of surgical space 400 may include a composition of imagery of subsurface anatomy 410 within aligned region 418 as captured by the second imaging modality and a feature of imagery of surface anatomy 408 within aligned region 418 as captured by the first imaging modality. For instance, system 100 may extract gradient information from the imagery of surface anatomy 408 within aligned region 418 and generate slope imagery representing the extracted gradient information. System 100 may modify the imagery of subsurface anatomy 410 within aligned region 418 as captured by the second imaging modality with the slope imagery, such as by summing the extracted slope imagery and the imagery of subsurface anatomy 410 within aligned region 418 as captured by the second imaging modality to generate a composition for the representation of the second portion of surgical space 400 in the composite image. As described, the composition may provide a visually realistic representation of depth of subsurface anatomy 410 relative to surface anatomy 408 in the composite image.

In certain examples, the combining of the slope imagery extracted from imagery of surface anatomy 408 with the imagery of subsurface anatomy 410 may be performed using actual, organic color values of the imagery of surface anatomy 408 and/or subsurface anatomy 410, without using artificial or non-photorealistic colors. This may contribute to the visually realistic representation of the surgical space, including the visually realistic representation of depth of subsurface anatomy 410 relative to surface anatomy 408 in the composite image.

Figure 5A:
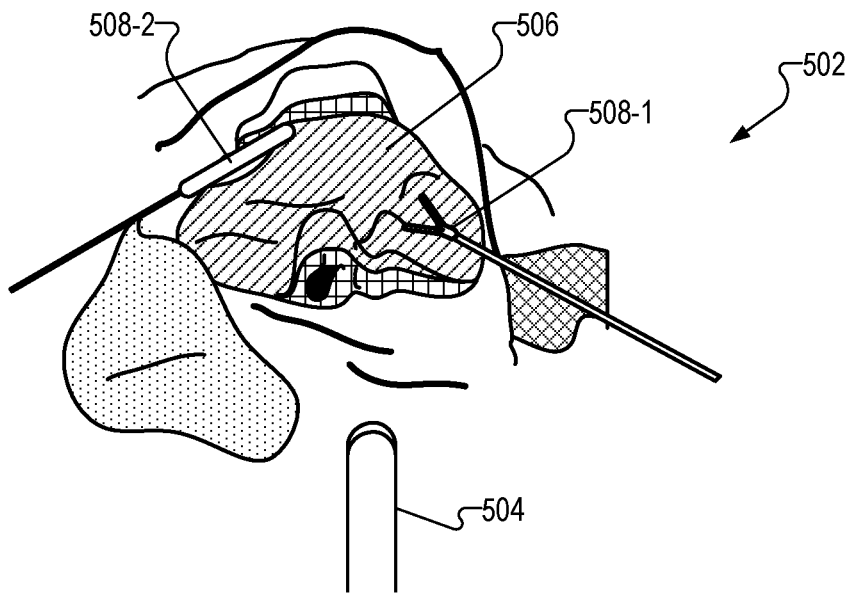
FIG. 5A illustrates an exemplary real workspace included in a surgical space according to principles described herein.

An exemplary way of generating a composite image of a surgical space will now be described. FIG. 5A illustrates a real workspace 502 that may be included in a surgical space. The real workspace 502 may be a real-world physical workspace located in front of an endoscope 504 configured to capture endoscopic imagery of the workspace. In certain examples, the real workspace 502 may include anatomy 506 of a patient and one or more surgical instruments 508 (e.g., surgical instruments 508-1 and 508-2) positioned relative to anatomy 506 in the real workspace 502. In the illustrated example, surgical instrument 508-1 is a grasper tool, and surgical instrument 508-2 is an ultrasound probe.

Figure 5B:
FIG. 5B illustrates an exemplary endoscopic image of the real workspace of FIG. 5A according to principles described herein.

System 100 may access a real image of the real workspace 502. For example, system 100 may access a real image of the real workspace 502 as captured by endoscope 504. FIG. 5B illustrates an example of a real image (R) of the real workspace 502 as captured by endoscope 504.

System 100 may generate a slope image from real image (R). For example, system 100 may extract gradient information from real image (R) and use the extracted gradient information to generate a slope image that represents the gradient information extracted from real image (R). The gradient information may represent directional change in a feature of real image (R), such as a directional change in intensity, color, or another feature of real image (R). The gradient information may represent change in one or more directions.

Figure 5C:
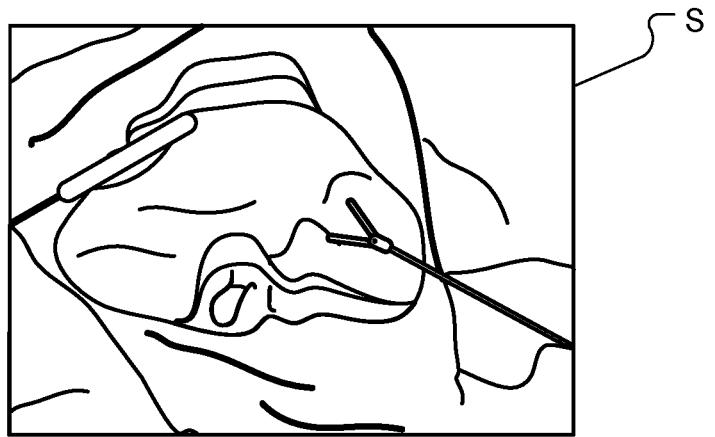
FIG. 5C illustrates an exemplary slope image extracted from the endoscopic image of FIG. 5B according to principles described herein.

FIG. 5C illustrates an example of a slope image (S) extracted from real image (R). Slope image (S) is illustrated in black and white in FIG. 5C. However, slope image (S) may include black, white, and/or gray in various shades that represent degrees of slope. Slope image (S) may represent any suitable gradient information, including horizontal gradient, vertical gradient, one or more other directional gradients, or any combination or sub-combination thereof.

System 100 may generate and maintain a virtual workspace representative of the real workspace 502. The virtual workspace may be a 3D space (e.g., a 3D coordinate space) to which imagery of the real workspace 502 as captured by different imaging modalities may be mapped. For example, endoscopic imagery captured by endoscope 504 and other imagery captured by one or more other imaging modalities may be mapped to the virtual workspace such that the endoscopic imagery and the other imagery are registered to one another in the virtual workspace.

The registration may be performed in any suitable way. For example, depth values may be determined and associated with pixels in real image (R) to generate a 3D mesh of 3D coordinate points that are associated with color values of the pixels. The 3D mesh may be mapped to the virtual workspace.

In examples in which other imagery captured by another imaging modality includes a 3D model of a surgical space, system 100 may map the 3D model to the virtual workspace. This may be performed in any suitable way and may include system 100 registering features in the 3D model to matching features of the 3D mesh generated from endoscopic imagery and depth information associated with the endoscopic imagery. Accordingly, the 3D model may be registered to the 3D mesh in the virtual workspace.

In examples in which other imagery captured by another imaging modality includes a 2D image of a surgical space and depth data for the 2D image is available, system 100 may map the 2D image to the virtual workspace similarly to how system 100 maps endoscopic imagery to the virtual workspace. In examples in which other imagery captured by another imaging modality includes a 2D image of a surgical space but depth data for the 2D image is unavailable, system 100 may project the 2D image to any suitable surface in the virtual workspace, such as the surface of a virtual object representing an augmentation region in the virtual workspace.

Figure 6A:
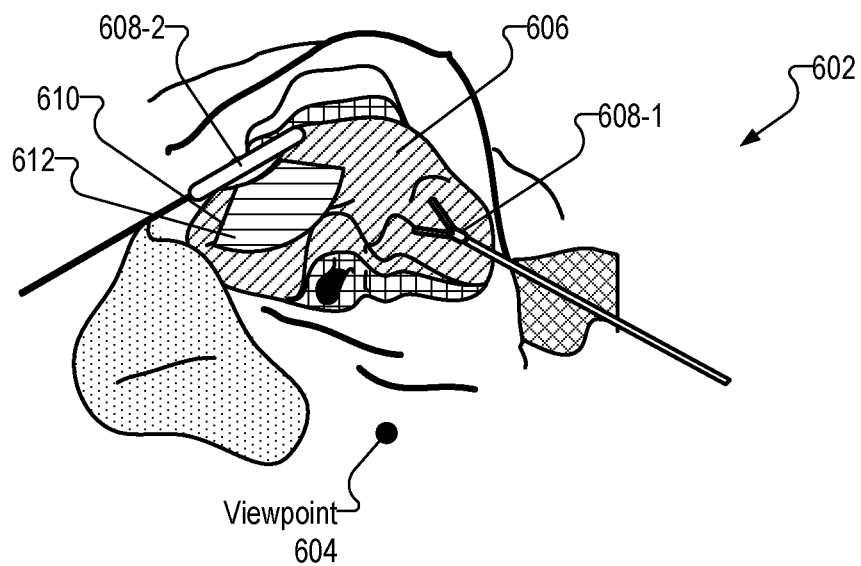
FIG. 6A illustrates an exemplary virtual workspace according to principles described herein.

FIG. 6A illustrates an exemplary virtual workspace 602 that may be generated by system 100 based on and/or representative of the real workspace 502. The virtual workspace 602 may include virtual representations of elements of the real workspace 502, such as a virtual representation 606 of anatomy 506 and virtual representations 608 (e.g., virtual representations 608-1 and 608-2) of surgical instruments 508 (e.g., surgical instruments 508-1 and 508-2). System 100 may generate the virtual representations in the virtual workspace in any suitable way, including based on real image (R) of the real workspace 502 and depth information associated with real image (R).

The virtual workspace 602 may also include an image render viewpoint 604 ("viewpoint 604"), which may be a virtual viewpoint corresponding to the viewpoint of endoscope 504 included in the real workspace 502. Viewpoint 604 may be configured based on intrinsic and extrinsic properties of endoscope 504. Viewpoint 604 may be positioned relative to other elements of the virtual workspace 602 and may represent a viewpoint perspective from which an image of the virtual workspace 602 may be rendered.

The virtual workspace 602 may also include an augmentation region 610 positioned relative to other elements of the virtual workspace 602. In the example illustrated in FIG. 6A, the position of augmentation region 610 is determined based on ultrasound probe 608-2 by projecting augmentation region 610 from ultrasound probe 608-2 in a particular manner (e.g., in a particular direction, orientation, pose, shape, etc.) such that augmentation region 610 is positioned relative to ultrasound probe 608-2, viewpoint 604, and other elements of the virtual workspace 602.

System 100 may project imagery captured by ultrasound probe 608-2 onto augmentation region 610 in the virtual workspace 602. The ultrasound imagery projected onto augmentation region 610 is represented by horizontal-line fill pattern 612 in FIG. 6A. While the example illustrated in FIG. 6A depicts a projection of ultrasound imagery onto augmentation region 610, any other imagery captured by another imaging modality may be projected onto augmentation region 610 in the virtual workspace 602. For example, system 100 may determine a slice of a 3D model (e.g., a 3D model generated from CT or MRI imagery) based on a position of augmentation region 610 relative to the 3D model registered to the virtual workspace 602 and project an image of the slice onto augmentation region 610. In such an example, augmentation region 610 projected from ultrasound probe 608-2 may function as a placeholder onto which an image of a slice of a registered 3D model of the surgical space 602 may be projected in the virtual workspace 602.

In certain examples, an image that is projected onto augmentation region 610 in the virtual workspace may be selected by way of user input to a computer-assisted surgical system. For example, a user of the computer-assisted surgical system may provide input to toggle from one imaging modality image being projected onto augmentation region 610 to another imaging modality image being projected onto augmentation region 610 (e.g., from an ultrasound image to a CT or MRI model image or vice versa).

Figure 6B:
FIG. 6B illustrates an exemplary image of the virtual workspace of FIG. 6A according to principles described herein.

System 100 may be configured to use the virtual workspace 602 in any suitable way to generate a composite image of the surgical space. For example, system 100 may generate an image of the virtual workspace 602 from the perspective of viewpoint 604. FIG. 6B illustrates an example of an image (V), which may be referred to as a virtual image (V), of the virtual workspace 602 rendered by system 100 from the perspective of viewpoint 604. As described herein, system 100 may be configured to use virtual image (V) to generate a composite image of the surgical space.

Figure 6C:
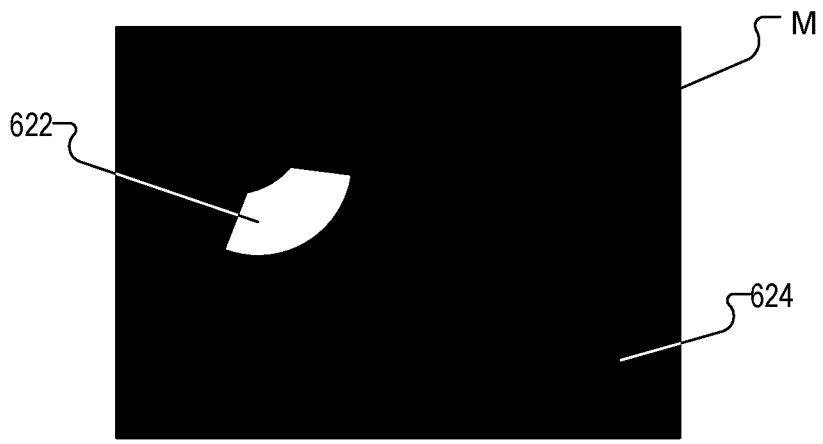
FIG. 6C illustrates an exemplary mask image according to principles described herein.

System 100 may generate a mask image such as a binary render mask image based on the virtual workspace 602 and/or virtual image (V). The mask image may correspond in size to virtual image (V) and may include a first portion that is aligned with the position of augmentation region 610 (e.g., an area inside of augmentation region 610) and that is assigned a first binary value, and a second portion that is not aligned with the position of augmentation region 610 (e.g., an area outside of augmentation region 610) and that is assigned a second binary value different from the first binary value. FIG. 6C illustrates an example of a mask image (M) that may be generated by system 100 based on virtual image (V). As shown, mask image (M) includes a first portion 622 including a white fill representing one binary value, and a second portion 624 including a black fill representing another binary value.

System 100 may be configured to use real image (R), slope image (S), virtual image (V), and mask image (M) to generate a composite image (C) of the surgical space. For example, system 100 may perform a blend function that generates a composite image (C) based on the real image (R), slope image (S), virtual image (V), and mask image (M). In certain implementations, the following blend function may be performed by system 100 for i, j iterating over the image width and height, respectively:

$$C=\text{blend}(R,S,V,M)=M_{(i,j)}*(S_{(i,j)}+V_{(i,j)})+(1-M_{(i,j)})*R_{(i,j)}$$

In this blend function, mask image (M) may have a binary value of "1" in a first portion that is aligned with augmentation region 610 and a binary value of "0" in a second portion that is not aligned with augmentation region 610. Accordingly, system 100 may use real image (R) for all pixel locations that are set to "0" in mask image (M) and may use a blended output of virtual image (V) and slope image (S) for all pixel locations that are set to "1" in mask image (M).

Based on this blend function, the first portion of the composite image (C) may include a representation of the surgical scene as captured by endoscope 504, and the second portion of the composite image (C) may include a representation of the surgical scene as captured by another imaging modality. The representation of the second portion of the surgical scene as captured by another imaging modality may include a composition of imagery of the surgical space as captured by the other imaging modality and a feature of the endoscopic imagery of the surgical space. For instance, to produce the representation of the second portion of the surgical space, system 100 may combine the imagery of the second portion of the surgical space as captured by the other imaging modality (e.g., this may include the imagery as mapped to the augmentation region 610 in the virtual workspace 602 and/or as represented in virtual image (V)) and slope imagery representing gradient information extracted from the endoscopic imagery of the second portion of the surgical space. This combination may be performed by system 100 executing the blend function iterating over the pixel locations of the composite image (C) and selectively using values at corresponding pixel locations in real image (R), slope image (S), virtual image (V), and mask image (M), as indicated by the blend function, to generate the composite image (C). In certain examples, this may be performed without using artificial colors to generate composite image (C).

Figure 7:
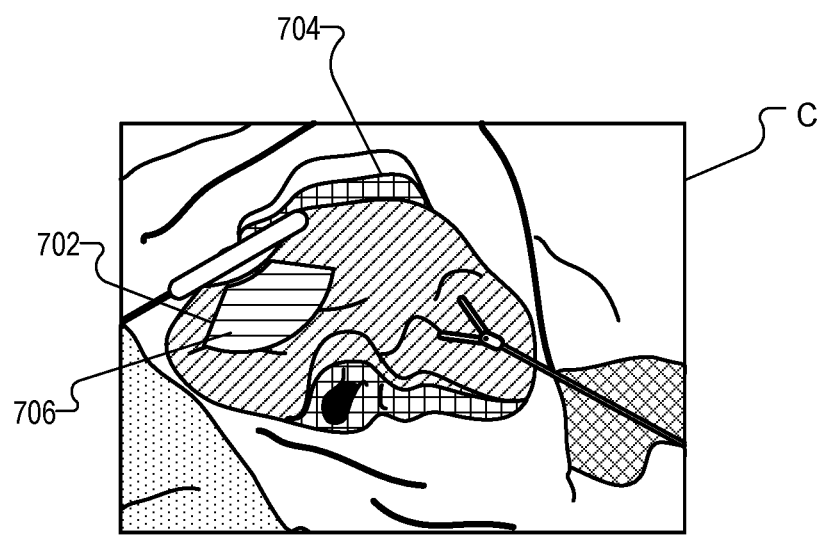
FIG. 7 illustrates an exemplary composite image of a surgical space according to principles described herein.

FIG. 7 illustrates an example of a composite image (C) that may be generated by system 100 performing a blend function to generate composite image (C) based on the real image (R), slope image (S), virtual image (V), and mask image (M). As shown, composite image (C) may include a representation 702 of augmentation region 610. Outside the representation 702 of augmentation region 610, composite image (C) includes a representation 704 of a first portion of the surgical space, which representation includes endoscopic imagery of surface anatomy as captured by endoscope 504. Inside the representation 702 of augmentation region 610, composite image (C) includes a representation 706 of a second portion of the surgical space as captured by another imaging modality (e.g., an ultrasound probe), which representation includes a composition of imagery captured by the other imaging modality and a feature of the endoscopic imagery (e.g., a slope of the endoscopic imagery) of the second region of the surgical space.

A composite image, such as composite image (C), may include any suitable representation of an augmentation region. Such a representation may include any visual representation of a boundary or transition between representations of first and second portions of a surgical scene in the composite image.

While FIG. 5A-FIG. 7 illustrate an example in which a first imaging modality includes an endoscope and a second imaging modality includes an ultrasound probe, images as captured by other different imaging modalities may be similarly processed to generate a composite image of a surgical space. In other examples, for instance, a first imaging modality may include an endoscope, and a second imaging modality may include a CT or MRI machine. In such examples, images may be captured by the CT or MRI machine during a preoperative phase of a surgical procedure and processed to generate a 3D model of the surgical space. System 100 may register the 3D model of the surgical space to the endoscopic imagery of the surgical space in a virtual workspace. System 100 may determine a position of an image render viewpoint relative to the surgical space, determine a position of an augmentation region relative to the surgical space, and use the position of the image render viewpoint and the position of the augmentation region relative to the surgical space to identify an image of the 3D model (e.g., a planar slice of the 3D image) to be used to generate a representation of the surgical space within the augmentation region. For example, system 100 may project the identified image of the 3D model onto the augmentation region in the virtual workspace and perform a blend function as described herein to generate a composite image of the surgical space.

In certain implementations, for example, system 100 may project an augmentation region from an ultrasound probe positioned in the surgical space. To this end, system 100 may access tracking information (e.g., position information, orientation information, movement information, kinematic information, etc.) for the ultrasound probe from a computer-assisted surgical system to which the ultrasound probe is connected and use the tracking information to identify a pose of the ultrasound probe (e.g., a position and an orientation of the ultrasound probe) within the surgical space. System 100 may project the augmentation region into the surgical space (e.g., into a virtual workspace representing a real workspace within the surgical space) based on the pose of the ultrasound probe.

In certain examples, system 100 may generate a composite image of the surgical space that includes, within the augmentation region, a representation of ultrasound imagery of the surgical space as captured by the ultrasound probe. In other examples, system 100 may generate a composite image of the surgical space that includes, within the augmentation region, a representation of a portion of the surgical space as captured by a different imaging modality. For example, the representation within the augmentation region may include or may be based on CT or MRI imagery of the surgical space (e.g., a 3D model of the surgical space generated from CT or MRI imaging of the surgical space). In such an example, the augmentation region projected from the ultrasound probe may function as a virtual cut-away region and/or a placeholder on which to project the CT-based or MRI-based representation of the surgical space. Accordingly, a user of a computer-assisted surgical system may provide input to position the ultrasound probe within the surgical space to select a position of the augmentation region to define a portion of the surgical space to be augmented with an image of a registered 3D model of the surgical space. As mentioned, in certain examples, system 100 may be configured to toggle the representation within the augmentation region between representing the ultrasound imagery as captured by the ultrasound probe and representing other imagery as captured by another imaging modality (e.g., CT or MRI imagery captured by a CT or MRI machine).

Use of an ultrasound probe to define and move an augmentation region relative to the surgical space is illustrative of certain examples. Other examples may implement a different real-world surgical instrument, a virtual object, or any other suitable mechanism to be used by a user to define and move an augmentation region relative to the surgical space.

As mentioned, system 100 may be implemented in or communicatively coupled to a computer-assisted surgical system. System 100 may receive input from and provide output to the computer-assisted surgical system. For example, system 100 may access imagery of a surgical space and/or any information about the surgical space and/or the computer-assisted surgical system from the computer-assisted surgical system, use the accessed imagery and/or information to perform any of the processing described herein to generate composite imagery of the surgical space, and provide data representative of the composite imagery to the computer-assisted surgical system for display (e.g., by a display device associated with the computer-assisted surgical system).

Figure 8:
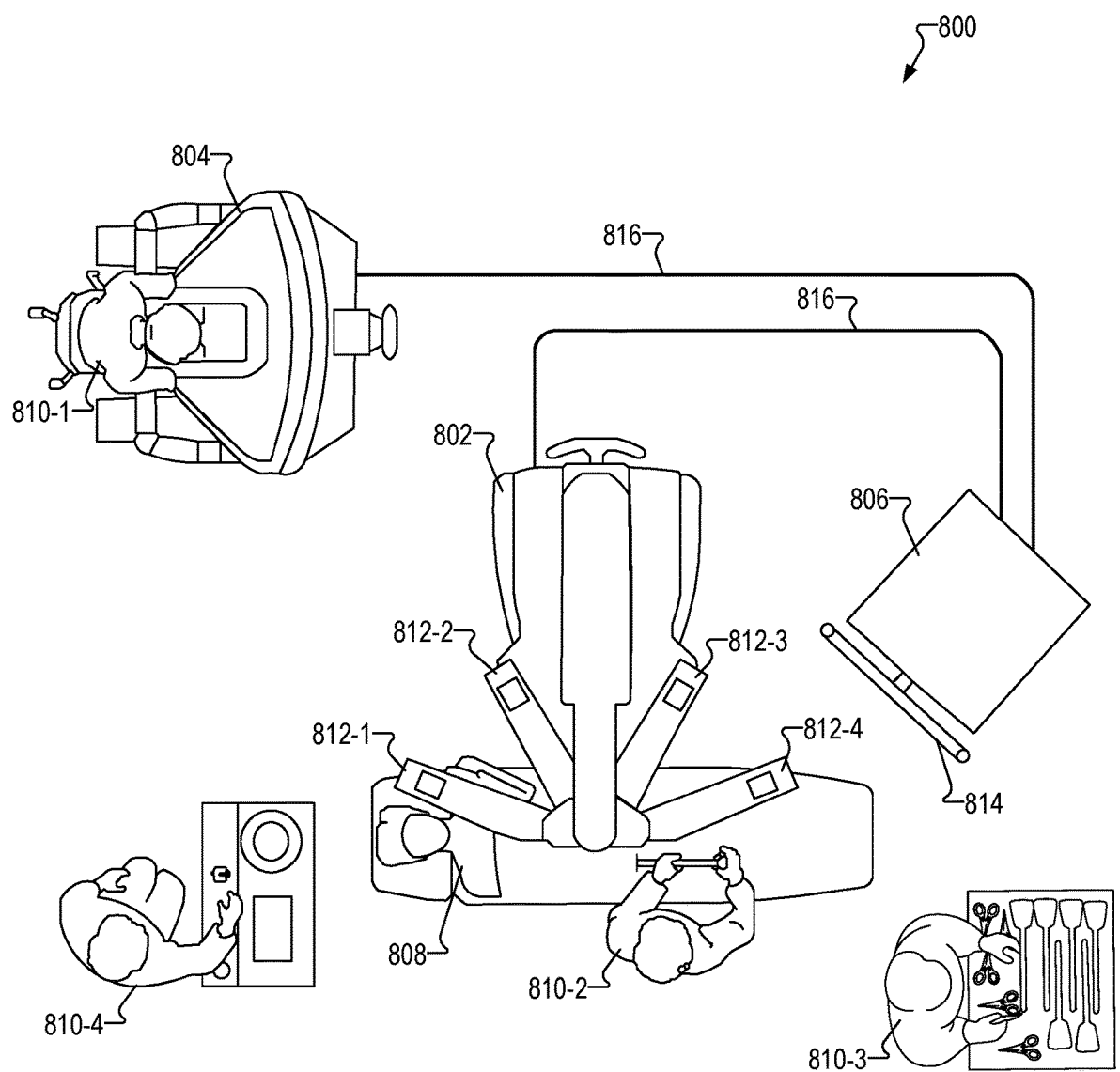
FIG. 8 illustrates an exemplary computer-assisted surgical system according to principles described herein.

FIG. 8 illustrates an exemplary computer-assisted surgical system 800 ("surgical system 800"). System 100 may be implemented by surgical system 800, connected to surgical system 800, and/or otherwise used in conjunction with surgical system 800.

As shown, surgical system 800 may include a manipulating system 802, a user control system 804, and an auxiliary system 806 communicatively coupled one to another. Surgical system 800 may be utilized by a surgical team to perform a computer-assisted surgical procedure on a patient 808. As shown, the surgical team may include a surgeon 810-1, an assistant 810-2, a nurse 810-3, and an anesthesiologist 810-4, all of whom may be collectively referred to as "surgical team members 810." Additional or alternative surgical team members may be present during a surgical session as may serve a particular implementation.

While FIG. 8 illustrates an ongoing minimally invasive surgical procedure, it will be understood that surgical system 800 may similarly be used to perform open surgical procedures or other types of surgical procedures that may similarly benefit from the accuracy and convenience of surgical system 800. Additionally, it will be understood that the surgical session throughout which surgical system 800 may be employed may not only include an operative phase of a surgical procedure, as is illustrated in FIG. 8, but may also include preoperative, postoperative, and/or other suitable phases of the surgical procedure.

As shown in FIG. 8, manipulating system 802 may include a plurality of manipulator arms 812 (e.g., manipulator arms 812-1 through 812-4) to which a plurality of surgical instruments may be coupled. Each surgical instrument may be implemented by any suitable surgical tool (e.g., a tool having tissue-interaction functions), medical tool, imaging device (e.g., an endoscope, an ultrasound tool, etc.), sensing instrument (e.g., a force-sensing surgical instrument), diagnostic instrument, or the like that may be used for a computer-assisted surgical procedure on patient 808 (e.g., by being at least partially inserted into patient 808 and manipulated to perform a computer-assisted surgical procedure on patient 808). While manipulating system 802 is depicted and described herein as including four manipulator arms 812, it will be recognized that manipulating system 802 may include only a single manipulator arm 812 or any other number of manipulator arms as may serve a particular implementation.

Manipulator arms 812 and/or surgical instruments attached to manipulator arms 812 may include one or more displacement transducers, orientational sensors, and/or positional sensors used to generate raw (i.e., uncorrected) kinematics information. One or more components of surgical system 800 may be configured to use the kinematics information to track (e.g., determine positions of) and/or control the surgical instruments.

User control system 804 may be configured to facilitate control by surgeon 810-1 of manipulator arms 812 and surgical instruments attached to manipulator arms 812. For example, surgeon 810-1 may interact with user control system 804 to remotely move or manipulate manipulator arms 812 and the surgical instruments. To this end, user control system 804 may provide surgeon 810-1 with imagery (e.g., high-definition 3D imagery) of a surgical space associated with patient 808 as captured by an imaging system (e.g., any of the medical imaging systems described herein). In certain examples, user control system 804 may include a stereo viewer having two displays where stereoscopic images of a surgical space associated with patient 808 and generated by a stereoscopic imaging system may be viewed by surgeon 810-1. In certain examples, composite imagery generated by the system 100 may be displayed by user control system 804. Surgeon 810-1 may utilize the imagery displayed by user control system 804 to perform one or more procedures with one or more surgical instruments attached to manipulator arms 812.

To facilitate control of surgical instruments, user control system 804 may include a set of master controls. These master controls may be manipulated by surgeon 810-1 to control movement of surgical instruments (e.g., by utilizing robotic and/or teleoperation technology). The master controls may be configured to detect a wide variety of hand, wrist, and finger movements by surgeon 810-1. In this manner, surgeon 810-1 may intuitively perform a procedure using one or more surgical instruments.

Auxiliary system 806 may include one or more computing devices configured to perform primary processing operations of surgical system 800. In such configurations, the one or more computing devices included in auxiliary system 806 may control and/or coordinate operations performed by various other components (e.g., manipulating system 802 and user control system 804) of surgical system 800. For example, a computing device included in user control system 804 may transmit instructions to manipulating system 802 by way of the one or more computing devices included in auxiliary system 806. As another example, auxiliary system 806 may receive, from manipulating system 802, and process image data representative of imagery captured by an imaging device attached to one of manipulator arms 812.

In some examples, auxiliary system 806 may be configured to present visual content to surgical team members 810 who may not have access to the images provided to surgeon 810-1 at user control system 804. To this end, auxiliary system 806 may include a display monitor 814 configured to display one or more user interfaces, such as images (e.g., 2D images) of the surgical space, information associated with patient 808 and/or the surgical procedure, and/or any other visual content as may serve a particular implementation. For example, display monitor 814 may display images of the surgical space (e.g., composite images generated by system 100) together with additional content (e.g., graphical content, contextual information, etc.) concurrently displayed with the images. In some embodiments, display monitor 814 is implemented by a touchscreen display with which surgical team members 810 may interact (e.g., by way of touch gestures) to provide user input to surgical system 800.

Manipulating system 802, user control system 804, and auxiliary system 806 may be communicatively coupled one to another in any suitable manner. For example, as shown in FIG. 8, manipulating system 802, user control system 804, and auxiliary system 806 may be communicatively coupled by way of control lines 816, which may represent any wired or wireless communication link as may serve a particular implementation. To this end, manipulating system 802, user control system 804, and auxiliary system 806 may each include one or more wired or wireless communication interfaces, such as one or more local area network interfaces, Wi-Fi network interfaces, cellular interfaces, etc.

Figure 9:
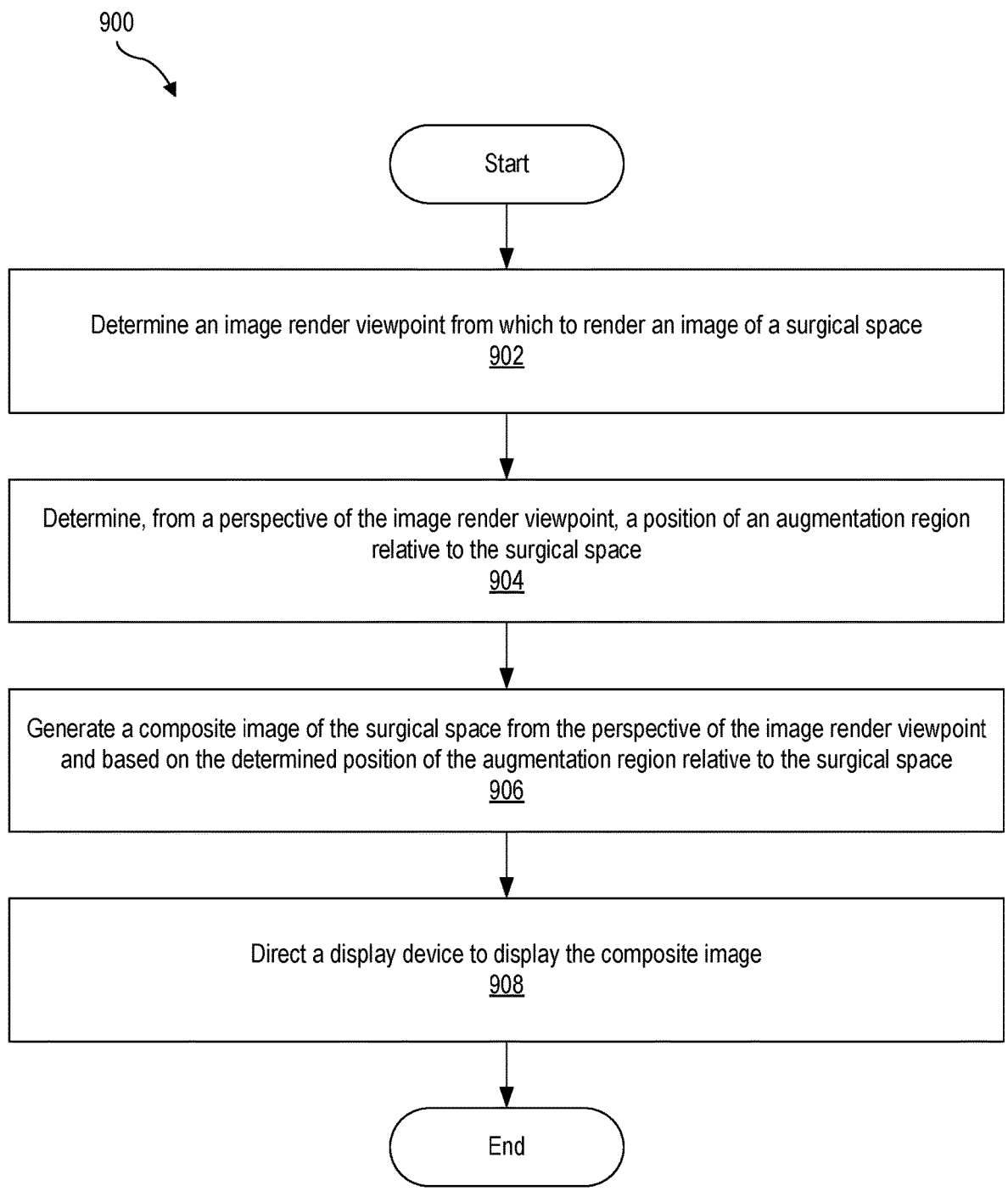
FIG. 9 illustrates an exemplary method according to principles described herein.

FIG. 9 shows an exemplary method 900. While FIG. 9 illustrates exemplary operations according to one embodiment, other embodiments may omit, add to, reorder, combine, and/or modify any of the steps shown in FIG. 9 One or more of the operations shown in in FIG. 9 may be performed by a computing system such as system 100, any components included therein, and/or any implementation thereof.

In operation 902, a computing system determines an image render viewpoint from which to render an image of a surgical space. Operation 902 may be performed in any of the ways described herein.

In operation 904, the computing system determines, from a perspective of the image render viewpoint, a position of an augmentation region relative to the surgical space. Operation 904 may be performed in any of the ways described herein.

In operation 906, the computing system generates a composite image of the surgical space from the perspective of the image render viewpoint and based on the determined position of the augmentation region relative to the surgical space. Operation 906 may be performed in any of the ways described herein.

In operation 908, the computing system directs a display device to display the composite image. Operation 908 may be performed in any of the ways described herein.

The composite image generated in operation 806 may be generated in any suitable way, including in any of the ways described herein. The composite image may include any of the exemplary elements described herein. For example, the composite image may include the augmentation region at the determined position of the augmentation region relative to the surgical space. Outside the augmentation region, the composite image may include a representation of a first portion of the surgical space as captured by a first imaging modality. Inside the augmentation region, the composite image may include a representation of a second portion of the surgical space as captured by a second imaging modality.

As described herein, the representation of a first portion of the surgical space as captured by a first imaging modality may include and/or may be generated based on the first imagery of the surgical space captured by the first imaging modality (e.g., an endoscope), and the representation of the second portion of the surgical space may be generated based on the first imagery of the surgical space captured by the first imaging modality and the second imagery of the surgical space captured by the second imaging modality (e.g., an ultrasound probe, a CT device, or an MRI device). For example, as described herein, the representation of the second portion of the surgical space may include a composition of the second imagery of the surgical space captured by the second imaging modality and a feature of the first imagery of the surgical space captured by the first imaging modality.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 10:
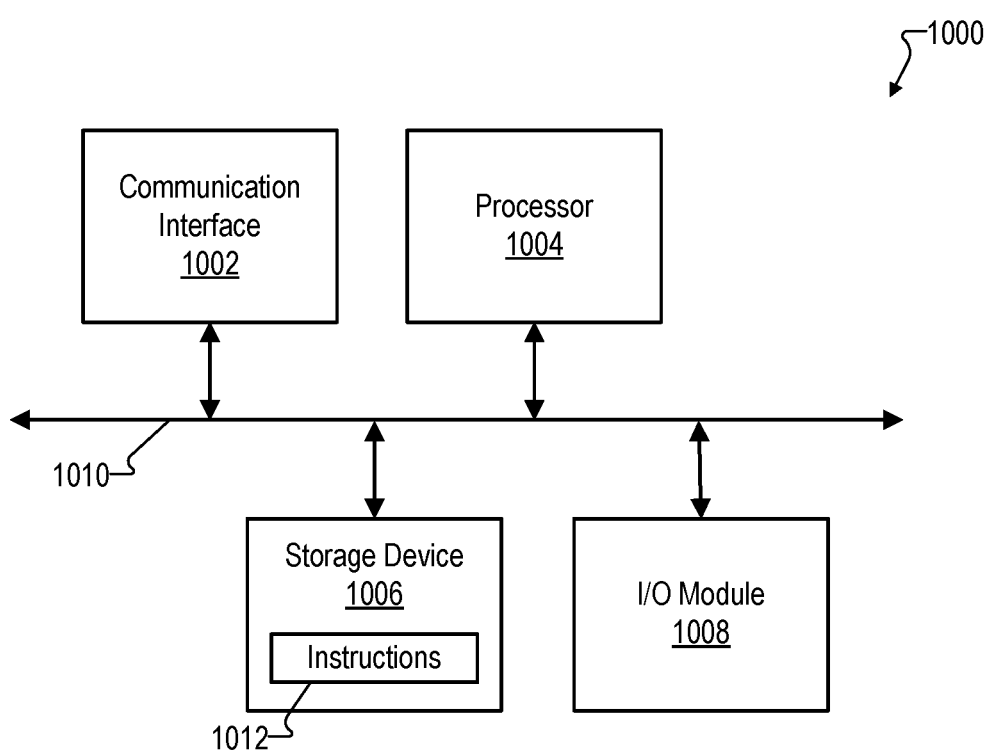
FIG. 10 illustrates an exemplary computing device according to principles described herein.

FIG. 10 illustrates an exemplary computing device 1000 that may be specifically configured to perform one or more of the processes described herein. Any of the systems, units, computing devices, and/or other components described herein may be implemented by computing device 1000.

As shown in FIG. 10, computing device 1000 may include a communication interface 1002, a processor 1004, a storage device 1006, and an input/output ("I/O") module 1008 communicatively connected one to another via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data and/or interpreting, executing, and/or directing execution of one or more of the instructions, processes, and/or operations described herein. Processor 1004 may perform operations by executing computer-executable instructions 1012 (e.g., an application, software, code, and/or other executable data instance) stored in storage device 1006.

Storage device 1006 may include one or more data storage media, devices, or configurations and may employ any type, form, and combination of data storage media and/or device. For example, storage device 1006 may include, but is not limited to, any combination of the non-volatile media and/or volatile media described herein. Electronic data, including data described herein, may be temporarily and/or permanently stored in storage device 1006. For example, data representative of computer-executable instructions 1012 configured to direct processor 1004 to perform any of the operations described herein may be stored within storage device 1006. In some examples, data may be arranged in one or more databases residing within storage device 1006.

I/O module 1008 may include one or more I/O modules configured to receive user input and provide user output. I/O module 1008 may include any hardware, firmware, software, or combination thereof supportive of input and output capabilities. For example, I/O module 1008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
generate a composite image of a surgical space from a perspective of an image render viewpoint and based on a position of an augmentation region relative to the surgical space, the composite image comprising:
the augmentation region at the position of the augmentation region relative to the surgical space,
outside the augmentation region, a representation of a first portion of the surgical space as captured by a first imaging modality, and inside the augmentation region, a representation of a second portion of the surgical space, the representation of the second portion generated based on gradient information extracted from first imagery of the surgical space captured by the first imaging modality and applied to modify second imagery of the surgical space captured by a second imaging modality; and direct a display device to display the composite image.

2. The system of claim 1, wherein the gradient information represents directional change in intensity or color of the first imagery.

3. The system of claim 1, wherein the gradient information extracted from the first imagery is applied to modify the second imagery by summing the second imagery and slope imagery representing the gradient information extracted from the first imagery.

4. The system of claim 1, wherein the gradient information is extracted from a portion of the first imagery that is within the augmentation region.

5. The system of claim 1, wherein:
the first imagery comprises imagery of surface anatomy included in the first portion of the surgical space; and
the second imagery comprises imagery of subsurface anatomy included in the second portion of the surgical space.

6. The system of claim 1, wherein:
the representation of the first portion of the surgical space comprises endoscopic imagery of surface anatomy included in the first portion of the surgical space;
the gradient information extracted from the first imagery comprises gradient imagery extracted from endoscopic imagery of surface anatomy included in the second portion of the surgical space; and
the representation of the second portion of the surgical space comprises a composition of
imagery of subsurface anatomy included in the second portion of the surgical space, and
slope imagery representing the gradient information extracted from the endoscopic imagery of the surface anatomy included in the second portion of the surgical space.

7. The system of claim 1, wherein:
the first imaging modality comprises an endoscopic imaging modality; and
the second imaging modality comprises one of an ultrasound imaging modality, a computerized tomography (CT) imaging modality, or a magnetic resonance imaging (MRI) imaging modality.

8. The system of claim 1, wherein:
the first portion of the surgical space is unaligned with the augmentation region from the perspective of the image render viewpoint; and
the second portion of the surgical space is aligned with the augmentation region from the perspective of the image render viewpoint.

9. The system of claim 1, wherein the augmentation region is projected from a surgical instrument that is selectively movable relative to the surgical space based on user input to a computer-assisted surgical system.

10. The system of claim 1, wherein:
the augmentation region is projected from an ultrasound probe that is selectively movable relative to the surgical space based on user input to a computer-assisted surgical system;
the first imagery comprises endoscopic imagery of the surgical space; and the second imagery comprises a slice image of a three-dimensional (3D) model generated from preoperative computerized tomography (CT) imagery or preoperative magnetic resonance imaging (MRI) imagery of the surgical space.

11. The system of claim 1, wherein the generating of the composite image comprises:
generating a virtual workspace representative of a real workspace included in the surgical space, the virtual workspace including
the first imagery of the surgical space captured by the first imaging modality and mapped to the virtual workspace,
the second imagery of the surgical space captured by the second imaging modality and mapped to the virtual workspace,
a virtual viewpoint representing the image render viewpoint mapped to the virtual workspace, and
a virtual object representing the augmentation region and positioned relative to the first imagery, the second imagery, and the virtual viewpoint in the virtual workspace; and
using the virtual workspace to generate the composite image of the surgical space.

12. The system of claim 11, wherein the using of the virtual workspace to generate the composite image of the surgical space comprises:
generating a virtual image of the virtual workspace;
generating a slope image representing the gradient information extracted from the first imagery of the surgical space; and
combining a portion of the virtual image of the virtual workspace and a corresponding portion of the slope image to generate the representation of the second portion of the surgical space.

13. A system comprising:
a memory storing instructions; and
a processor communicatively coupled to the memory and configured to execute the instructions to:
generate a composite image of a surgical space based on first imagery captured by a first imaging modality and second imagery captured by a second imaging modality different from the first imaging modality, the composite image comprising:
a representation of a first portion of the surgical space, the representation of the first portion of the surgical space generated based on the first imagery captured by the first imaging modality,
an augmentation region integrated within the representation of the first portion of the surgical space, and
inside the augmentation region, a representation of a second portion of the surgical space, the representation of the second portion generated based on a composition of the second imagery that is within the augmentation region and gradient information extracted from the first imagery that is within the augmentation region, wherein the gradient information is applied to modify the second imagery; and
direct a display device to display the composite image.

14. The system of claim 13, wherein the composition is generated based on actual, organic colors included in the first imagery that is within the augmentation region and the second imagery that is within the augmentation region, without using artificial colors.

15. A method comprising:
generating, by a computing system, a composite image of a surgical space from a perspective of an image render viewpoint and based on a position of an augmentation region relative to the surgical space, the composite image comprising:
  the augmentation region at the position of the augmentation region relative to the surgical space,
  outside the augmentation region, a representation of a first portion of the surgical space as captured by a first imaging modality, and
  inside the augmentation region, a representation of a second portion of the surgical space, the representation of the second portion generated based on gradient information extracted from first imagery of the surgical space captured by the first imaging modality and applied to modify second imagery of the surgical space captured by a second imaging modality; and
directing, by the computing system, a display device to display the composite image.

16. The method of claim 15, wherein:
the representation of the first portion of the surgical space comprises endoscopic imagery of surface anatomy included in the first portion of the surgical space;
the gradient information extracted from the first imagery comprises gradient imagery extracted from endoscopic imagery of surface anatomy included in the second portion of the surgical space; and
the representation of the second portion of the surgical space comprises a composition of
  imagery of subsurface anatomy included in the second portion of the surgical space, and
  slope imagery representing the gradient information extracted from the endoscopic imagery of the surface anatomy included in the second portion of the surgical space.

17. The method of claim 15, wherein the augmentation region is projected from a surgical instrument that is selectively movable relative to the surgical space based on user input to a computer-assisted surgical system.

18. The method of claim 15, wherein:
the augmentation region is projected from an ultrasound probe that is selectively movable relative to the surgical space based on user input to a computer-assisted surgical system;
the first imagery comprises endoscopic imagery of the surgical space; and
the second imagery comprises a slice image of a three-dimensional (3D) model generated from preoperative computerized tomography (CT) imagery or preoperative magnetic resonance imaging (MRI) imagery of the surgical space.

19. The method of claim 15, wherein the gradient information represents directional change in color of the first imagery.

20. The method of claim 15, wherein the gradient information represents directional change in intensity of the first imagery.

* * * * *